United States Patent [19]
Becher et al.

[11] 4,232,172
[45] Nov. 4, 1980

[54] PROCESS FOR THE PREPARATION OF 3,6-DICHLORO-SALICYCLIC

[75] Inventors: Manfred Becher, Bingen; Richard Sehring, Ingelheim am Rhein, both of Fed. Rep. of Germany

[73] Assignee: Celamerck GmbH & Co. KG, Ingelheim am Rhein, Fed. Rep. of Germany

[21] Appl. No.: 878,074

[22] Filed: Feb. 15, 1978

[30] Foreign Application Priority Data

Mar. 5, 1977 [DE] Fed. Rep. of Germany ....... 2709721

[51] Int. Cl.³ .............................................. C07C 51/15
[52] U.S. Cl. .................................... 562/423; 562/424; 562/477
[58] Field of Search .................... 260/521 C; 562/423, 562/424

[56] References Cited

U.S. PATENT DOCUMENTS 1,891,677  12/1932  Laska et al. .......................... 562/424

FOREIGN PATENT DOCUMENTS

| 70274 | 5/1915 | Austria | 562/424 |
| 43-11211 | 5/1968 | Japan | 562/424 |
| 45-13328 | 5/1970 | Japan | 502/424 |
| 46-10933 | 3/1971 | Japan | 260/521 C |
| 7014328 | 4/1971 | Netherlands | 260/521 C |

*Primary Examiner*—Paul J. Killos
*Attorney, Agent, or Firm*—Hammond, Littell, Weissenberger & Muserlian

[57] ABSTRACT

An improved process for the preparation of 3,6-dichlorosalicylic acid by carboxylation of potassium 2,5-dichlorophenolate with carbon dioxide in xylene at elevated pressure, where the improvement consists of adding finely powdered, anhydrous potassium carbonate to the reaction mixture, whereby the yield of 3,6-dichloro-salicylic acid is significantly increased.

3 Claims, No Drawings

PROCESS FOR THE PREPARATION OF 3,6-DICHLORO-SALICYCLIC

This invention relates to a novel improvement in the process for the preparation of 3,6-dichloro-salicylic acid by carboxylation of potassium 2,5-dichloro-phenolate with carbon dioxide in xylene at elevated pressure.

THE PRIOR ART

U.S. Pat. No. 3,013,054 discloses a process for the preparation of 3,6-dichloro-salicylic acid which consists of carboxylating potassium 2,5-dichloro-phenolate with carbon dioxide in xylene at elevated pressure. The yield of the desired end product is about 29% of theory.

OBJECT OF THE INVENTION

It is an object of the present invention significantly to improve the prior art process with respect to the yield of the desired end product.

Other objects and advantages of the invention will become apparent as the description thereof proceeds.

DESCRIPTION OF THE INVENTION

We have discovered that the yield of 3,6-dichlorosalicylic acid obtained by carboxylating potassium 2,5-dichloro-phenolate with carbon dioxide in xylene at elevated pressure is markedly improved by adding an effective yield-improving amount of finely powdered potassium carbonate to the reaction mixture. For instance, we have found that the yield of 3,6-dichloro-salicylic acid is doubled by adding 1.5 mols of very finely powdered potassium carbonate per mol of 2,5-dichloro-phenol to the reaction mixture pursuant to U.S. Pat. No. 3,013,054, but not otherwise altering the prior art process. If the potassium carbonate added to the reaction mixture is somewhat less finely comminuted, then a larger amount of potassium carbonate, up to about 2 mols per mol of 2,5-dichloro-phenol, has the same advantageous effect.

Instead of pure 2,5-dichloro-phenol, a mixture of 2,5-dichloro-phenol and other, isomeric dichlorophenols may also be used as the starting material for the improved process of the present invention. For example, when technical grade dichloro-phenol consisting of about 81% 2,5-dichloro-phenol, 15% 2,4-dichlorophenol and 3% other isomers is used as the starting material in our improved process, the percentage distribution of the corresponding isomeric dichlorosalicylic acids in the carboxylation product is substantially the same as in the starting material, and the total yield of dichloro salicylic acids is also about 60% of theory.

3,6-Dichloro-salicylic acid is a known compound and is useful for the preparation of 2-methoxy- 3,6-dichloro-benzoic acid (Dicamba), a known herbicide, by methylating the phenolic OH-group (see U.S. Pat. No. 3,297,427). For this process the potassium salt of 3,6-dichloro-salicylic acid, which is the initial product of the carboxylation process, can be used without having to isolate the free acid first. The mixture of isomeric dichlorosalicylic acids or of their sodium salts obtained by carboxylating technical grade dichlorophenol may also be directly subjected to the methylation process.

The following examples illustrate the present invention and will enable others skilled in the art to understand it more completely. It should be understood, however, that the invention is not limited solely to the particular examples given below.

EXAMPLE 1

A solution of 81.5 gm (0.50 mol) of 2,5-dichlorophenol in 400 ml of xylene was boiled with 31.8 gm of 88% caustic potash (corresponding to 0.50 mol KOH) in a vessel equipped with an efficient water trap comprising a water-cooled phase separation tube until no more water separated out of the distillate. An anhydrous solution of potassium 2,5-dichlorophenolate in xylene was thus obtained. This solution was filtered and then charged into a shaker autoclave having a capacity of 2 liters, which had been warmed to 40° C. 104 gm (0.75 mol) of finely powdered, anhydrous potassium carbonate were then added to the contents, and the autoclave was flushed with carbon dioxide and then closed. The contents of the autoclave were now shaken for 25 minutes at 40° C. while introducing carbon dioxide at a pressure of 40 bars. Thereafter, the introduction of carbon dioxide was discontinued, and the contents of the autoclave were shaken at 140° C. for 15 hours, whereby the internal pressure rose to 70–80 bars. The contents of the autoclave were now allowed to cool to below 60° C., the pressure was released, and the autoclave was subsequently emptied by first rinsing it with xylene and then with a total of 700 ml of water. The xylene phases, including the solid matter contained therein, were combined. The solid matter was separated from the xylene mother liquor by suction filtration and then dissolved in the aqueous phase. The aqueous solution thus obtained was made strongly acid with concentrated hydrochloric acid, whereupon 3,6-dichloro-salicylic acid precipitated out. The precipitate was collected by suction filtration and, together with three liters of water, subjected to steam distillation. Any dichlorophenol and xylene still present passed over with the steam, whereas the desired product remained in the distillation vessel. When the distillate passing over was clear, the distillation was stopped. The contents of the distillation vessel were now filtered while still hot, and the filtrate was cooled, whereupon the product crystallized out. It was collected by suction filtration and dried (1st product fraction).

The insoluble matter contained in the hot aqueous distillate was separated and boiled with 1 liter of water; tar-like components remained undissolved and were filtered off. The filtrate thus obtained was combined with the mother liquor of the 1st product fraction, and this solution was evaporated to dryness. The residue was recrystallized from water and dried, yielding a 2nd product fraction which had the same melting point as the 1st product fraction. Total yield: 62.2 gm (0.30 mol; 60% of theory) of 3,6-dichloro-salicylic acid, m.p. 193°–195° C.

About 25% of the starting material was recovered from the filtered xylene mother liquor of the reaction mixture.

EXAMPLE 2

The process described in Example 1 was repeated using the same amounts of starting material, solvent and caustic potash, but no potassium carbonate was added to the reaction mixture. The total yield of 3.6-dichlorosalicylic acid was 32.8 gm (0.58 mol; 31.7% of theory), m.p. 192°–195° C.

EXAMPLE 3

The process described in Example 1 was repeated using the same amount of starting material and solvent, but no potassium carbonate was added to the reaction mixture, and a 25% excess of potassium hydroxide was provided for the potassium salt formation. Total yield of 3,6-dichloro-salicylic acid: 19.5 gm (0.094 mol; 18.8% of theory), m.p. 190°–194° C. This comparative example shows that the yield of 3,6-dichloro-salicylic acid is reduced rather than increased by providing an excess of potassium hydroxide available for potassium salt formation.

EXAMPLE 4

The process described in Example 1 was repeated, but in place of pure 2,5-dichloro-phenol the same amount of a distilled technical grade dichlorophenol mixture of the following composition
81% 2,5-dichloro-phenol
15% 2,4-dichloro-phenol
3% other dichlorophenols
was used as the starting material. The processing of the reaction mixture was modified as follows:

The contents of the distillation vessel which remained therein after completion of the steam distillation were filtered, whereby tar-like components were separated from the aqueous solution. The filtrate was made strongly acid with concentrated hydrochloric acid, whereupon a portion of the reaction product precipitated out, and the precipitate was collected by suction filtration (1st product fraction). The filtrate was evaporated to dryness in vacuo, and the residue was treated with 250 ml of boiling absolute ethanol, whereby the organic components went into solution while the inorganic salt components remained undissolved. The insoluble matter was filtered off, and the filtrate was evaporated to dryness in vacuo, leaving another fraction of the reaction product (2nd product fraction). The two product fractions were combined and homogenized by trituration. Total yield: 62.8 gm (0.30 mol; 60% of theory). Melting point range: about 175°–180° C.

After recrystallization from water, the product had the following composition (determined by gas-chromatography):
87.7% 3,6-dichloro-salicylic acid
12.3% 3,5-dichloro-salicylic acids.

About 30% of the starting material was recovered from the filtered mother liquor of the reaction mixture.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the apended claims.

We claim:
1. The method of increasing the yield of 3,6-dichloro-salicylic acid in a process comprising carboxylating potassium 2,5-dichloro-phenolate with carbon dioxide in xylene at elevated pressure, which consist of adding an effective yield-increasing amount of finely powdered, anhydrous potassium carbonate to the carboxylation reaction mixture.

2. The method of claim 1, where the amount of potassium carbonate added is from 1 to 2 mols per mol of 2,5-dichloro-phenol.

3. The method of claim 1, wherein the amount of potassium carbonate added is from 1.2 to 1.8 mols per mol of 2,5-dichloro-phenol.

* * * * *